United States Patent [19]

Haley

[11] Patent Number: 5,233,735
[45] Date of Patent: Aug. 10, 1993

[54] EMBALMING INSTRUMENT CART

[76] Inventor: Reginald J. Haley, 1030 Cumberland Ct., Waldorf, Md. 20601

[21] Appl. No.: 811,939

[22] Filed: Dec. 23, 1991

[51] Int. Cl.$^5$ ............................................. A61G 17/00
[52] U.S. Cl. ....................................... 27/21.1; 5/507.1; 5/658; 27/23.1
[58] Field of Search .................... 27/21.1, 23.1, 28; 5/503.1, 507.1, 600, 658

[56] References Cited

U.S. PATENT DOCUMENTS

| | | |
|---|---|---|
| 830,532 | 9/1906 | Rozee . |
| 1,542,699 | 6/1925 | Jones . |
| 2,228,727 | 1/1944 | Pain . |
| 2,733,110 | 1/1956 | Berner et al. . |
| 2,906,575 | 9/1959 | Schlackman et al. . |
| 3,080,835 | 3/1963 | Guglielmi . |
| 3,548,910 | 8/1969 | Ritchey . |
| 3,854,155 | 12/1974 | Picard . |
| 4,113,218 | 9/1978 | Linder . |
| 4,720,881 | 1/1988 | Meyers ............................ 5/503.1 X |
| 4,747,172 | 5/1988 | Hohol et al. . |
| 4,843,690 | 7/1989 | Iacboucci et al. ................... 27/21.1 |
| 4,980,956 | 1/1991 | Fischer et al. . |
| 4,982,481 | 1/1991 | Deutscher ............................ 27/21.1 |
| 5,093,969 | 3/1992 | McGuire ............................. 27/21.1 |

*Primary Examiner*—Richard E. Chilcot, Jr.
*Attorney, Agent, or Firm*—Wigman, Cohen, Leitner & Myers

[57] ABSTRACT

An embalming instrument cart for use in association with an embalming table is disclosed. The cart generally comprises two pairs of vertical support members spaced by a horizontal tray each of adequate length and width such that the device can straddle the embalming table and roll from one end to the other. The horizontal tray is provided with a functional sink for bathing the deceased and disinfecting instruments required for embalming; a light source which can be focussed on the area of the decedent being treated; a means for supporting an irrigation hose; and a plurality of compartments to accommodate bottles of chemicals, disinfecting solutions, instruments, and cosmetics typically used during the embalming process.

18 Claims, 2 Drawing Sheets

EMBALMING INSTRUMENT CART

BACKGROUND OF THE INVENTION

1. Field of the Invention

This invention relates to an apparatus for carrying out embalming procedures. More particularly, the invention relates to an embalming instrument cart which provides the user with easy access to the instruments, chemicals, and other tools used during the embalming process.

2. Description of the Prior Art

Embalming is a long practiced procedure performed to preserve the physical appearance of a dead body by treatment with preservatives. Each year hundreds of thousands of embalmings are carried out in funeral homes, hospital pathology laboratories, medical examiner's offices and academic and research institutions. The procedure generally requires the use of a variety of instruments, chemicals, disinfecting solutions and cosmetics. As the mortician or embalmer works on different parts of the body, different tools and chemicals are required. Typically, these materials are stored away on shelves and in cabinets in the embalming room, requiring the mortician to frequently leave the work area to acquire new materials and equipment or replace existing tools. This practice creates the risk of an embalming error; it is often time consuming and cumbersome; and it is violative of some religious customs which require the decedent to remain attended at all times. Moreover, the fact that many embalmers work without staff assistance creates a further need for having embalming tools and chemicals within easy reach.

Additionally, during the embalming process it is necessary to bathe the dead body and rinse the instruments with disinfecting solutions. However, embalming rooms usually are not provided with sinks at the work area, which necessitates repeated trips to nearby sinks, again jeopardizing and prolonging the embalming process.

A search of the prior art failed to uncover any devices suitable for use by an embalmer which would overcome the disadvantages of conventional techniques.

SUMMARY AND OBJECTS OF THE INVENTION

In view of the foregoing, it should be apparent that there is still a need in the art for a device which provides a mortician with instant access to the instruments and chemicals required in the embalming process; a device that prevents having to leave the corpse unattended; and that minimizes the time needed to perform the embalming procedures.

Accordingly, it is a primary object of this invention to provide an embalming apparatus and method which is highly efficient and which reduces the time required to perform an embalming procedure.

Another object of this invention is to provide an embalming instrument cart which is suitable for use in conjunction with embalming tables and which includes a plurality of compartments adapted to receive needed chemicals, disinfecting solutions, cosmetics, and instruments.

Still another object of this invention is to provide an embalming instrument cart which may easily be rolled from one end of the embalming table to the other so as to be positioned over the area wherein the embalming work is being carried out.

Yet another object of this invention is to provide an embalming instrument cart which includes a means for supporting an irrigation hose such that the hose is within easy reach of the mortician yet does not interfere with other embalming procedures.

A further object of this invention is to provide an embalming instrument cart which includes a functional sink for washing the dead body and disinfecting the embalming instruments.

A further object of this invention is to provide a light source which can be focussed on the area being treated.

These and other objects and advantages that may become apparent hereinafter are accomplished in accordance with this invention by providing an easily movable embalming instrument cart comprising two pairs of vertical support members spaced by a horizontal tray of sufficient length such that the device can straddle a typical embalming table. The horizontal tray is provided with a plurality of compartments sized and shaped to receive the bottles of chemicals and disinfecting solutions, instruments, and cosmetics typically used during the embalming process. The embalming instrument cart is further provided with a means for supporting an irrigation hose as well as a light.

With the foregoing and other objects, advantages and features of the invention that will become hereinafter apparent, the nature of the invention may be more clearly understood by reference to the following detailed description of the invention, the appended claims and to the several views illustrated in the attached drawings.

DETAILED DESCRIPTION OF A PREFERRED EMBODIMENT

Figure 1:
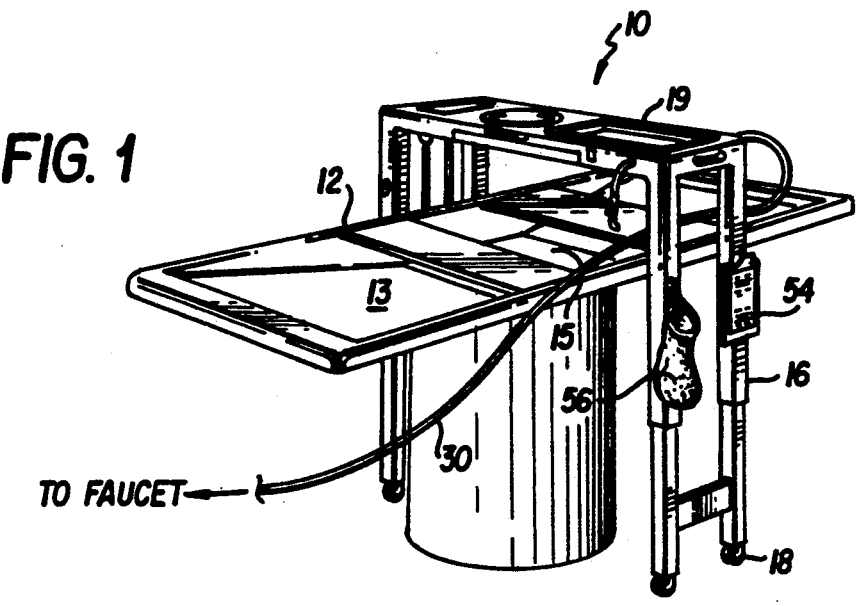
FIG. 1 is a perspective view of the embalming instrument cart of the present invention shown straddling an embalming table.

Referring now in detail to the drawings wherein like parts are designated by like reference numerals throughout, there is illustrated in FIG. 1 a perspective view of the embalming cart of the present invention designated generally by reference numeral 10. Cart 10 is shown straddling an embalming table 12 which generally comprises a horizontal bed portion 13 on which the body is placed during the embalming procedure. The bed portion 13 of table 12 has an upstanding rim or circumferential edge to contain bodily fluids and chemicals used to wash, rinse, or irrigate the body and to direct the liquid and solids towards the central portion 15 of the table where it is deposited into a drain positioned there below. Embalming cart 10, designed to facilitate the embalming process on table 12, generally comprises a horizontal tray 14 positioned above the table and defining compartments to retain the various items used during the procedure, adjustable legs 16, which allow the height of tray 14 to vary to accommodate the height of the embalming table and bodies of various sizes, an irrigation hose support, and a number of other features described below.

Figure 4:
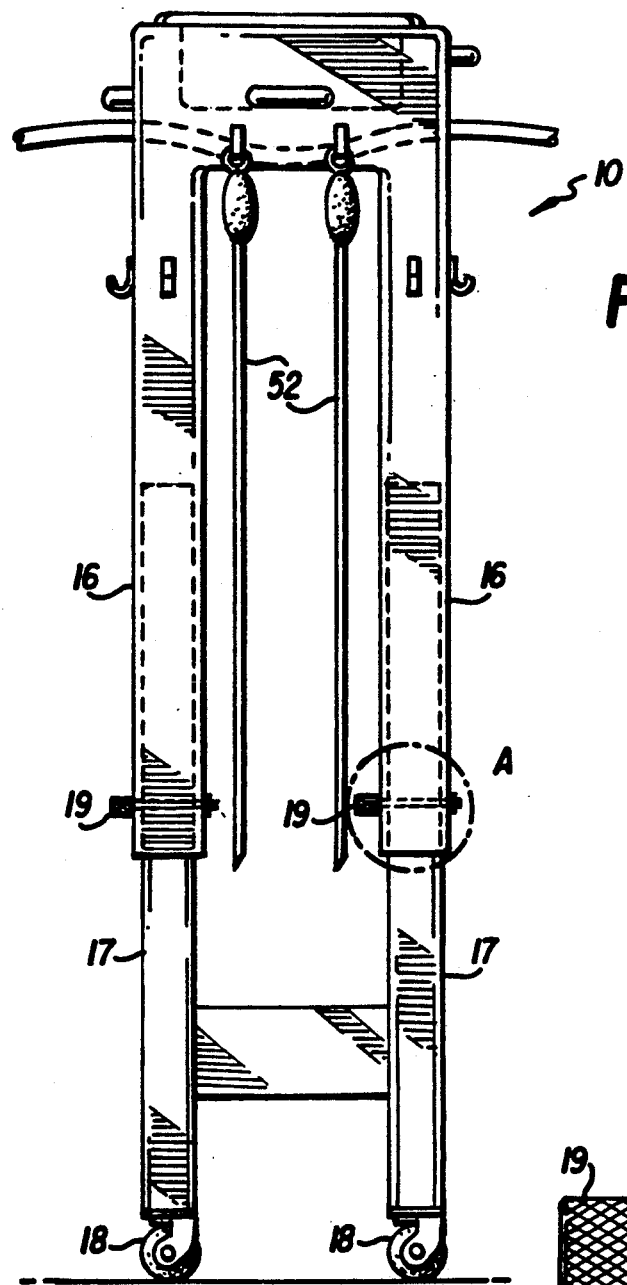
FIG. 4 is a side elevational view of the embalming instrument cart of the present invention.
Figure 5:
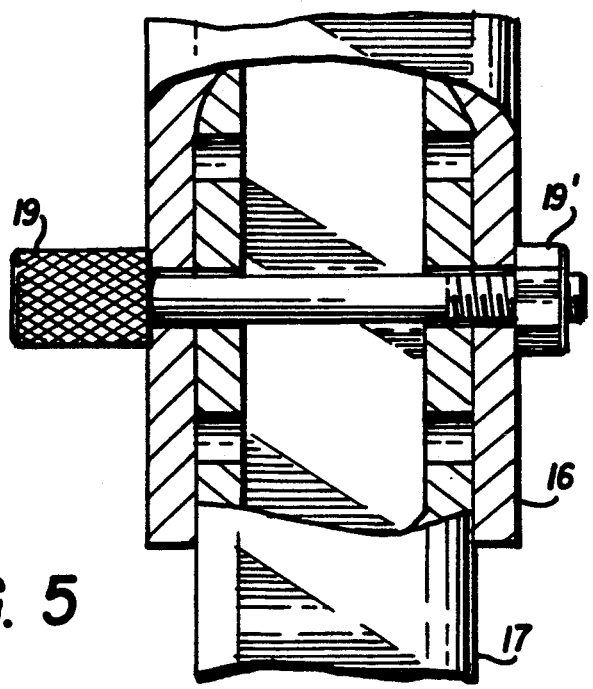
FIG. 5 is an enlarged sectional view showing the detail of the leg locking mechanism shown in FIG. 4.

More particularly, and with reference to FIG. 4, legs 16 are preferably constructed of metal but may optionally be constructed of wood or plastic. In the embodiment shown four legs are provided, however, the cart of the present invention may also be supported by a pair of legs mounted to a base (not shown), or any other suitable support. Preferably, legs 16 are provided with telescoping members 17 such that the height of the tray 14 may be varied depending on the height of the embalming table and the size of the corpse. Locking pins 19 project through apertures defined in legs 16 and members 17 to fix the legs in the desired position using a nut 19' as shown in FIG. 5. Alternatively, other locking devices, such as conventional spring biased locking pins (not shown) may be employed.

Casters 18 or other rollers are mounted to the bottom of the leg members 17 to allow the device to be easily transported along table 12 as the location of the work area changes.

Figure 2:
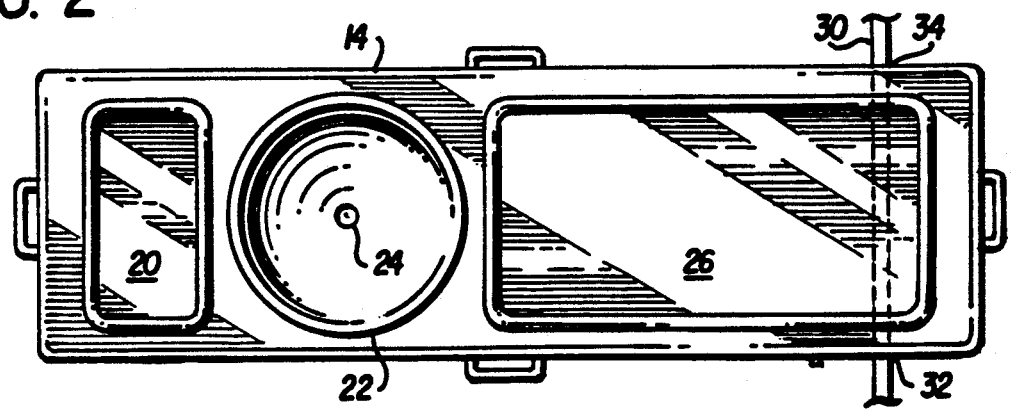
FIG. 2 is a top plan view of the embalming instrument cart of the present invention.
Figure 3:
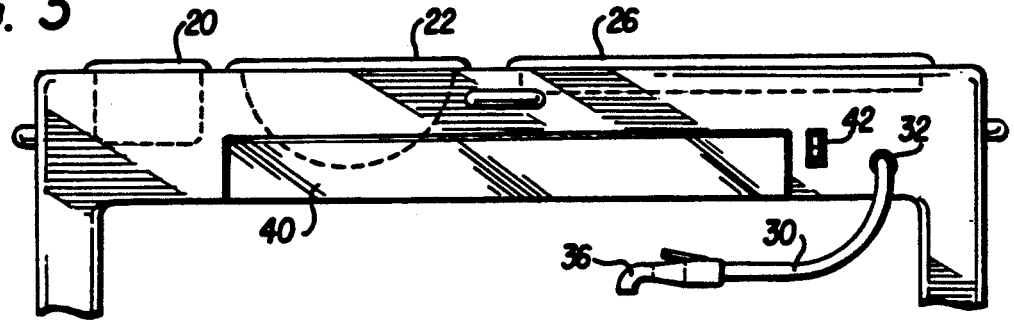
FIG. 3 is a partial front elevational view of the embalming instrument cart of the present invention.

With reference to FIGS. 2 and 3, horizontal tray 14 of cart 10 includes a plurality of removable containers to retain materials used in the embalming process. Compartments are formed in the upper surface of cart 10 to receive these containers. A first container 20, preferably constructed of plastic, is provided to hold, various bottles of embalming fluids and disinfectants in an upright position. A circular sink 22, made of metal, plastic, or ceramic, is provided to bathe the dead body and disinfect the instruments used in the procedure. An open drain 24 with a conventional stopper is provided. A rectangular tray 26 is provided to retain the various instruments used by the embalmer. Tray 26 is preferably constructed of plastic or metal.

As shown in FIGS. 1 and 3, an irrigation hose 30 is connected to a faucet (not shown) and passes through tray 14 via apertures 32, 34 where it emerges from the tray to overhang the table. A nozzle 36 is provided at the end of hose 30. Hose 30 and nozzle 36 are positioned such that they may be easily accessed by the mortician to rinse the corpse or may be used in association with sink 22 to bathe the corpse and disinfect the embalming instruments.

In FIG. 3, a fluorescent lamp 40 is mounted within a recess defined on the front face of tray 14 to direct concentrated light to the underlying work area. A conventional switch 42 is mounted on tray 14 to activate and deactivate lamp 40.

With reference to FIG. 4, the embalming instrument cart 10 is provided with a plurality of hooks 50 for holding equipment commonly used during the embalming process such as probes 52, a clipboard 54 and a waste receptacle 56 (FIG. 1).

The above-described invention allows its user to perform an embalming procedure conveniently, efficiently, and quickly. It is, in short, a self-contained, portable mortician's laboratory which places all of the conventional tools, chemicals, and equipment needed during an embalming procedure including disinfecting solutions and cosmetics as well as an irrigation hose and a concentrated light source in a position within easy reach of the mortician.

Although only a preferred embodiment of the invention is specifically illustrated and described herein, it will be appreciated that many modifications and variations of the invention are possible in light of the above teachings and within the purview of the appended claims without departing from the spirit and intended scope of the invention.

What is claimed is:

1. Embalming apparatus comprising:
   an embalming table for supporting a body in a generally horizontal position; and
   a movable cart comprising a plurality of compartments for holding embalming chemicals, instruments and the like; said movable cart including leg members which support said compartments above said table, and said cart including means for supporting an irrigation hose above said table.

2. The apparatus of claim 1 wherein said plurality of compartments comprise openings defined by the upper surface of said cart wherein a plurality of containers are removably positioned within said openings.

3. The apparatus of claim 2 wherein said plurality of containers includes a first and second generally rectangular container for holding instruments and bottles therein.

4. The apparatus of claim 2 wherein said plurality of containers includes a generally circular basin.

5. The apparatus of claim 1 further including wheels secured to the bottom of said legs for moving said cart freely from one end of the embalming table to the other.

6. The apparatus of claim 1 further including a light source for directing concentrated light to the site of the area being treated.

7. The apparatus of claim 1 wherein said embalming table comprises a generally horizontal bed portion for supporting the body, said bed portion having upstanding edges, a central portion for supporting said bed portion above the floor, wherein said central portion is provided with means for receiving drainage from the embalming procedure.

8. Embalming apparatus comprising:
   an embalming table for supporting a body in a generally horizontal position; and
   a movable cart comprising a plurality of compartments for holding embalming chemicals, instruments and the like; said movable cart including leg members which support said compartments above said table, and said cart including means for supporting an irrigation hose above said table, and further including a pair of apertures defined in opposite sides of said cart such that said hose may pass through said apertures and be supported thereby.

9. The apparatus of claim 1 wherein said legs are telescoping.

10. The apparatus of claim 9 and further including a lock for securing said telescoping legs.

11. A cart for use in conjunction with an embalming table comprising:
    a generally horizontal tray;
    at least one generally vertical member for supporting said tray above said table;
    a plurality of compartments defined by said tray for retaining materials used during an embalming procedure and, means for supporting an irrigation hose above said table.

12. The apparatus of claim 11 wherein said plurality of compartments comprise openings defined by the upper surface of said cart wherein a plurality of containers are removably positioned within said openings.

13. The apparatus of claim 12 wherein said plurality of containers includes a first and second generally rectangular container for holding instruments and bottles therein.

14. The apparatus of claim 12 wherein said plurality of containers includes a generally circular basin.

15. The apparatus of claim 11 and further including wheels secured to the bottom of said at least one generally vertical member for moving said cart freely from one end of the embalming table to the other.

16. The apparatus of claim 15 and further including a hose for irrigating the corpse and for washing the instruments in said basin.

17. The apparatus of claim 12 wherein said removable container are made of plastic, metal or glass.

18. A method for embalming comprising the steps of:

placing a body onto an embalming table;

moving a cart containing embalming fluids and instruments for carrying out the embalming procedure over said table and said body, said cart comprising a plurality of compartments for receiving said embalming fluids, disinfectants, tools and, means for supporting an irrigation hose above said table:

irrigating said body and washing said tools with said hose;

performing said embalming process; and, removing said cart from said table after completion of said embalming process.

* * * * *